US008377037B2

(12) United States Patent
Sachdeva et al.

(10) Patent No.: US 8,377,037 B2
(45) Date of Patent: *Feb. 19, 2013

(54) MEDICAL DEVICE WITH SLOTTED MEMORY METAL TUBE

(75) Inventors: Rohit C. L. Sachdeva, Plano, TX (US); Petrus A. Besselink, Enschede (NL)

(73) Assignee: EVM Systems LLC, Frisco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/267,512

(22) Filed: Oct. 6, 2011

(65) Prior Publication Data

US 2012/0022577 A1 Jan. 26, 2012

Related U.S. Application Data

(63) Continuation of application No. 11/381,217, filed on May 2, 2006, now Pat. No. 8,052,670, which is a continuation of application No. 10/923,918, filed on Aug. 23, 2004, now Pat. No. 7,037,321, which is a continuation of application No. 09/156,276, filed on Sep. 17, 1998, now Pat. No. 6,780,175, which is a continuation of application No. 08/804,018, filed on Feb. 21, 1997, now Pat. No. 5,885,258.

(60) Provisional application No. 60/012,220, filed on Feb. 23, 1996.

(51) Int. Cl.
*A61M 25/00* (2006.01)
*A61M 29/00* (2006.01)

(52) U.S. Cl. ......... 604/531; 604/530; 604/105; 606/200

(58) Field of Classification Search ................. 606/198, 606/200; 604/105, 530, 531
See application file for complete search history.

(56) References Cited

U.S. PATENT DOCUMENTS

| 3,799,172 A | 3/1974 | Szpur |
| 3,815,608 A | 6/1974 | Spinosa et al. |
| 3,890,977 A | 6/1975 | Wilson |
| 4,043,346 A | 8/1977 | Mobley et al. |
| 4,503,569 A | 3/1985 | Dotter |
| 4,512,338 A | 4/1985 | Balko et al. |
| 4,580,568 A | 4/1986 | Gianturco |
| 4,625,726 A | 12/1986 | Duthoy |

(Continued)

FOREIGN PATENT DOCUMENTS

| DE | 4136861 | 5/1993 |
| DE | 4223897 | 1/1994 |

(Continued)

OTHER PUBLICATIONS

Defendants' [Abbott Laboratories and Abbott Vascular, Inc.] Preliminary Invalidity Contentions Related to U.S. Patent No. 7,037,321, dated Jun. 9, 2011, in *EVM Systems LLC v. Cordis Corporation et al.*, United States District Court for the Eastern District of Texas, Case No. 6:10-cv-437 (LED).

(Continued)

*Primary Examiner* — Victoria P Shumate
(74) *Attorney, Agent, or Firm* — Martin & Ferraro, LLP

(57) ABSTRACT

A series of medical instruments can be made with the use of shape memory tube with a transformation temperature that is above or below the ambient temperature. In the first case, the material behaves with the shape memory effect and in the second case the behavior is superelastic. The wall of the tube has been provided with a plurality of slots in specific places, often near or at the distal end of the instrument, and in specific arrangements which allow local variations in diameter, shape, and/or length. These variations can either be caused by the memory effect during temperature change or by superelastic behavior during change of the mechanical influences on the memory metal by the surrounding material.

15 Claims, 4 Drawing Sheets

U.S. PATENT DOCUMENTS

| | | |
|---|---|---|
| 4,655,771 A | 4/1987 | Wallsten |
| 4,665,906 A | 5/1987 | Jervis |
| 4,706,671 A | 11/1987 | Weinrib |
| 4,732,152 A | 3/1988 | Wallsten et al. |
| 4,807,626 A | 2/1989 | McGirr |
| 4,808,163 A | 2/1989 | Laub |
| 4,830,003 A | 5/1989 | Wolff et al. |
| 4,865,017 A | 9/1989 | Shinozuka |
| 4,886,061 A | 12/1989 | Fischell et al. |
| 4,954,126 A | 9/1990 | Wallsten |
| 4,997,435 A | 3/1991 | Demeter |
| 5,019,090 A | 5/1991 | Pinchuk |
| 5,026,377 A | 6/1991 | Burton et al. |
| 5,053,009 A | 10/1991 | Herzberg |
| 5,057,114 A | 10/1991 | Wittich et al. |
| 5,061,275 A | 10/1991 | Wallsten et al. |
| 5,064,428 A | 11/1991 | Cope et al. |
| 5,064,434 A | 11/1991 | Haber |
| 5,074,871 A | 12/1991 | Groshong |
| 5,100,423 A | 3/1992 | Fearnot |
| 5,108,420 A | 4/1992 | Marks |
| 5,109,830 A | 5/1992 | Cho |
| 5,152,748 A | 10/1992 | Chastagner |
| 5,160,342 A | 11/1992 | Reger et al. |
| 5,171,314 A | 12/1992 | Dulebohn |
| 5,190,557 A | 3/1993 | Borodulin et al. |
| 5,193,533 A | 3/1993 | Body et al. |
| 5,197,978 A | 3/1993 | Hess |
| 5,201,740 A | 4/1993 | Nakao et al. |
| 5,211,651 A | 5/1993 | Reger et al. |
| 5,224,945 A | 7/1993 | Pannek, Jr. |
| 5,224,953 A | 7/1993 | Morgentaler |
| 5,230,621 A | 7/1993 | Jacoby |
| 5,232,440 A | 8/1993 | Wilk |
| 5,242,448 A | 9/1993 | Pettine et al. |
| 5,254,130 A | 10/1993 | Poncet et al. |
| 5,281,214 A | 1/1994 | Wilkins et al. |
| 5,281,236 A | 1/1994 | Bagnato et al. |
| 5,311,858 A | 5/1994 | Adair |
| 5,320,627 A | 6/1994 | Sorensen et al. |
| 5,324,284 A | 6/1994 | Imran |
| 5,330,482 A | 7/1994 | Gibbs et al. |
| 5,330,483 A | 7/1994 | Heaven et al. |
| 5,332,402 A | 7/1994 | Teitelbaum |
| 5,344,439 A | 9/1994 | Otten |
| 5,350,398 A | 9/1994 | Pavcnik et al. |
| 5,354,308 A | 10/1994 | Simon et al. |
| 5,354,309 A | 10/1994 | Schnepp-Pesch et al. |
| 5,376,100 A | 12/1994 | Levebvre |
| 5,382,261 A | 1/1995 | Palmaz |
| 5,397,320 A | 3/1995 | Essig et al. |
| 5,409,460 A | 4/1995 | Krumme |
| 5,415,637 A | 5/1995 | Khosravi |
| 5,421,955 A | 6/1995 | Lau et al. |
| 5,423,849 A | 6/1995 | Engelson et al. |
| 5,433,723 A | 7/1995 | Lindenberg et al. |
| 5,445,646 A | 8/1995 | Euteneuer et al. |
| 5,456,667 A | 10/1995 | Ham et al. |
| 5,496,277 A | 3/1996 | Termin et al. |
| 5,496,330 A | 3/1996 | Bates et al. |
| 5,499,995 A | 3/1996 | Teirstein |
| 5,501,694 A | 3/1996 | Ressemann et al. |
| 5,507,766 A | 4/1996 | Kugo et al. |
| 5,509,923 A | 4/1996 | Middleman et al. |
| 5,514,154 A | 5/1996 | Lau et al. |
| 5,522,822 A | 6/1996 | Phelps et al. |
| 5,534,007 A | 7/1996 | St. Germain et al. |
| 5,540,701 A | 7/1996 | Sharkey et al. |
| 5,540,712 A | 7/1996 | Kleshinski et al. |
| 5,540,713 A | 7/1996 | Schnepp-Pesch et al. |
| 5,545,210 A | 8/1996 | Hess et al. |
| 5,601,600 A | 2/1997 | Ton |
| 5,607,435 A | 3/1997 | Sachdeva et al. |
| 5,611,803 A | 3/1997 | Heaven et al. |
| 5,630,829 A | 5/1997 | Lauterjung |
| 5,637,089 A | 6/1997 | Abrams et al. |
| 5,643,312 A | 7/1997 | Fischell et al. |
| 5,643,313 A | 7/1997 | Levin |
| 5,658,296 A | 8/1997 | Bates et al. |
| 5,693,085 A | 12/1997 | Buirge et al. |
| 5,702,419 A | 12/1997 | Berry et al. |
| 5,707,362 A | 1/1998 | Yoon |
| 5,725,552 A | 3/1998 | Kotula et al. |
| 5,733,329 A | 3/1998 | Wallace et al. |
| 5,766,191 A | 6/1998 | Trerotola |
| 5,766,192 A | 6/1998 | Zacca |
| 5,846,248 A | 12/1998 | Chu et al. |
| 5,857,464 A | 1/1999 | Desai |
| 5,885,258 A | 3/1999 | Sachdeva et al. |
| 5,957,900 A | 9/1999 | Ouchi |
| 6,168,603 B1 | 1/2001 | Leslie et al. |
| 6,176,240 B1 | 1/2001 | Nikolchev et al. |
| 6,780,175 B1 | 8/2004 | Sachdeva et al. |
| 6,818,014 B2 | 11/2004 | Brown et al. |
| 7,037,321 B2 | 5/2006 | Sachdeva et al. |
| 2006/0206136 A1 | 9/2006 | Sachdeva et al. |

FOREIGN PATENT DOCUMENTS

| | | |
|---|---|---|
| EP | 0 512 729 A1 | 11/1992 |
| EP | 0 512 729 B1 | 11/1992 |
| EP | 0566280 | 10/1993 |
| WO | WO 92/14506 | 9/1992 |

OTHER PUBLICATIONS

Defendants' Boston Scientific's Invalidity Contentions and Disclosures Under Local Patent Rules 3-3 and 3-4 (including Exhibits (10 pages), Exhibit B (7 pages), and Exhibit C (19 pages)), dated Jun. 9, 2011, in *EVM Systems LLC v. Cordis Corporation et al.*, United States District Court for the Eastern District of Texas, Case No. 6:10-cv-437 (LED).

Besselink, Peter A., et al.; "Applications of Shape Memory Effects;" Journal de Physique IV, Colloque C8, supplement au Journal de Physique III, vol. 5; Dec. 1995, pp. 111-116.

Duerig, T.W., et al.; "The Use of Superelasticity in Medicine;" Metal—publication for trade, business, technology and science from Special Edition Issue 9/96, metal Verlag Huethig GmbH, Sep. 1996; cover page and pp. 569-574.

Declaration of John William Morris filed concurrently with Request for Ex Parte Reexamination of U.S. Patent No. 7,037,321, Reexamination Proceeding No. 90/009,876, Feb. 15, 2011.

Cope, C., Novel Nitinol Basket Instrument for Percutaneous Cholecystolithotomy, American Journal of Roentgenology, Technical Note, 155:515-516, Sep. 1990.

Office Action dated May 27, 2005, from prosecution history of U.S. Patent No. 7,037,321 to Sachdeva et al.

Amendment dated Oct. 18, 2005, from prosecution history of U.S. Patent No. 7,037,321 to Sachdeva et al.

Office Action dated Dec. 16, 2005, from prosecution history of U.S. Patent No. 7,037,321 to Sachdeva et al.

Schmitz-Rode, T. et al., Experimental Nonsurgical Female Sterilization: Transcervical Implantation of Microspindles in Fallopian Tubes, Journal of Vascular and Interventional Radiology, Nov.-Dec. 1994, pp. 905-910.

Schmitz-Rode, T. et al., Self-Expandable Spindle for Transcatheter Vascular Occlusion: In Vivo Experiments, Radiology, Jul. 1993; 188:95-100.

Amendment dated Jan. 10, 2006, from prosecution history of U.S. Patent No. 7,037,321 to Sachdeva et al.

Defendants' [Abbott Laboratories and Abbott Vascular, Inc.] Preliminary Invalidity Contentions Related to U.S. Patent No. 7,037,321, dated Jun. 9, 2011, in *EVM Systems LLC v. Cords Corporation et al.*, United States District Court for the Eastern District of Texas, Case No. 6:10-cv-437 (LED).

Defendants' Boston Scientific's Invalidity Contentions and Disclosures Under Local Patent Rules 3-3 and 3-4), dated Jun. 9, 2011, in *EVM Systems LLC v. Cordis Corporation et al.*, United States District Court for the Eastern District of Texas, Case No. 6:10-cv-437 (LED).

FIG. 7B  FIG. 7C *PRIOR ART*

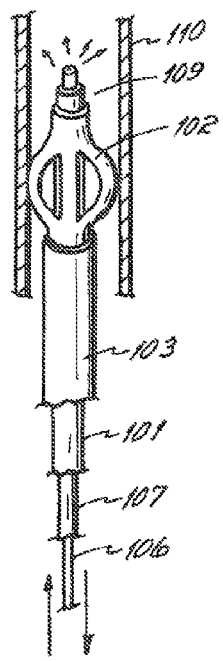
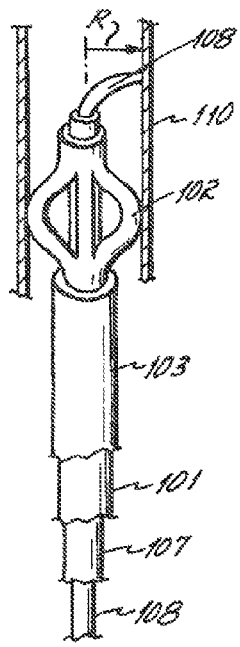
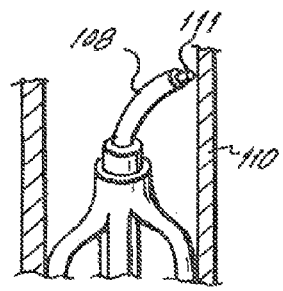
FIG.10A  FIG.10B  FIG.10C
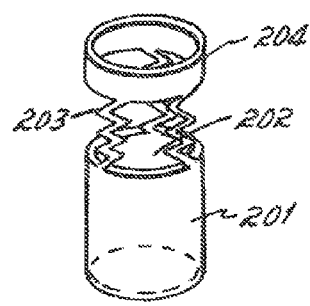
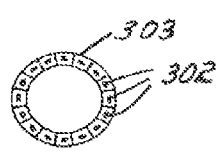
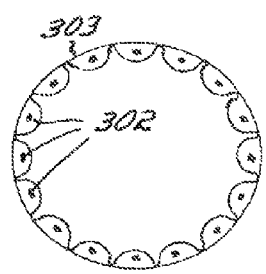
FIG.11  FIG.12A  FIG.12B

MEDICAL DEVICE WITH SLOTTED MEMORY METAL TUBE

The present application is a continuation of U.S. Ser. No. 11/381,217, filed May 2, 2006, now issued as U.S. Pat. No. 8,052,670, which is a continuation of U.S. Ser. No, 10/923,918, filed Aug. 23, 2004, now issued as U.S. Pat. No. 7,037,321, which is a continuation of U.S. Ser. No. 09/156,276, filed Sep. 17, 1998, now issued as U.S. Pat. No. 6,780,175, which is a continuation of U.S. Ser. No. 08/804,018, filed Feb. 21, 1997, now issued as U.S. Pat. No. 5,885,258, which claims the filing benefit of U.S. Provisional Application No. 60/012,220, filed Feb. 23, 1996, each disclosure of which is expressly incorporated herein by reference in its entirety.

FIELD OF THE INVENTION

This invention generally relates to an instrument which uses a slotted memory metal tube to perform or assist in various medical procedures.

BACKGROUND INFORMATION

Surgical and other medical procedures are often performed at sites within a patient's body. In the past, the only way to perform such medical procedures was to cut a large enough incision in the patient's body to expose the operating site sufficiently to permit direct access by a physician. Such operations, however, typically caused a great deal of trauma to the affected tissue requiring lengthy periods for recovery and causing the patient substantial pain and suffering. With technological advances in the medical profession, more and more of these procedures are being performed using less invasive endoscopic and similar procedures. In general, endoscopic procedures include using an instrument having a delivery tube with an inner bore through which a tool can be inserted. With such an instrument, the delivery tube is usually inserted into the patient's body by way of either a comparatively small incision or a body orifice and through a body cavity or hollow organ to the site desired. In this way, any trauma to the patient's body can be generally limited to surrounding tissue along the insertion path of the delivery tube.

Many procedures have been limited to traditional direct access methods due to the size and method of operation of the tools used to perform the procedures. As a result, there is a need for tools which are more adaptable to use with endoscopic and similar procedures.

OBJECTS OF THE INVENTION

One object of the invention is a medical instrument with slotted memory metal tube.

Another object of the invention is a retrieval basket for small particles.

A further object of the invention is a tool for dilating vessels and other tubular structures.

Yet another object of the invention is a device for reaming vascular, other tubular structures, or different shaped cavities.

Still a further object of the invention is a pump for injection of a defined quantity of fluid.

Yet a further object of the invention is an optical system with an expanding section which allows inspection of the expanded area.

Another object of the invention is an internal gripper for holding soft tissue such as skin, nerves, arteries, or the like or for holding clips.

Yet a further object of the invention is an external gripper for attaching to stems, tissue, or skin.

Still a further object of the invention is a tool for expanding cavities for inspection.

A further object of the invention is an expandable plug for closing a cavity or tubular structure.

Yet another object of the invention is a device for measuring the diameter of tubular structures.

Another object of the invention is a steerable catheter tip.

Still another object of the invention is a reinforced stent.

Additional objects, advantages, and novel features of the invention will be set forth in part in the description which follows, and in part will become apparent to those skilled in the art upon examination of the following description.

SUMMARY OF THE INVENTION

According to the present invention, the foregoing and other objects are attained by a medical instrument with slotted memory metal tube. A series of medical instruments can be made with the use of a shape memory tube with a transformation temperature that is above or below the ambient temperature. In the first case, the material behaves with the shape memory effect, and in the second case, the behavior is superelastic. Thus, the memory metal tube of the medical instrument is programmed for an effect selected from the group of effects consisting of memory effect and superelasticity.

In all of the disclosed types of instruments, the wall of the tube has been provided with a plurality of slots in specific places, often near or at the distal end of the instrument, and in specific arrangements, which allow local variations in diameter, shape, and/or length. These variations can either be caused by the memory effect during temperature change or by superelastic behavior during change of the mechanical influences on the memory metal by the surrounding material. One possibility to activate the superelastic shape change can be the use of a second tube, surrounding the memory metal tube, sliding more or less over the area where the slots in the memory metal tube are placed. The second tube is used to control the final shape and it prevents shape changes at undesired moments, such as during the procedure of insertion into the human body. The delivery tube can be pulled backward over the central memory metal tube. As soon as the memory metal tube comes free, it can regain its preprogrammed shape whether by superelasticity or by temperature change.

Dependent on the intended function of the device, the amount and pattern of slots in the wall of the memory metal tube can be chosen. The slots can be made by a variety of methods, such as, but not limited to, etching, spark erosion, water jet cutting, abrasive water jet cutting, laser cutting, or any mechanical means. An expansion of the slotted part of the desired programmed shape can be achieved by some internal or external mechanical means and, when the final heat treatment has been applied, the prestrained shape will be the new programmed shape. After removing the internal or external shaping tool, the memory metal tube is ready for use.

It is possible to make memory metal tubes which are deformed to a small diameter and which will return to a larger diameter in the slotted section by superelasticity or by shape memory effect. The reverse is also possible when the slotted section is opened to a larger diameter than the programmed diameter by some internal restraining means. It will return to a smaller diameter when it is released. The slotted section can be made in several places along the length of the memory metal tube and the programmed shapes can vary over the length of the tube.

BRIEF DESCRIPTION OF THE DRAWINGS

FIGS. 7A through 7D are partial sectional pictorial views of an external gripper of the present invention.

FIGS. 10A through 10C are partial sectional pictorial views of a measuring tip of the present invention.

FIG. 11 is a pictorial view of a steerable tip of the present invention.

FIGS. 12A and 12B are cross-sectional views of a reinforced stent of the present invention.

DESCRIPTION OF THE PREFERRED EMBODIMENTS

A series of examples will describe certain preferred embodiments of the present invention.

Retrieval Basket

Figures 1A, 1B, 1C, 1D:
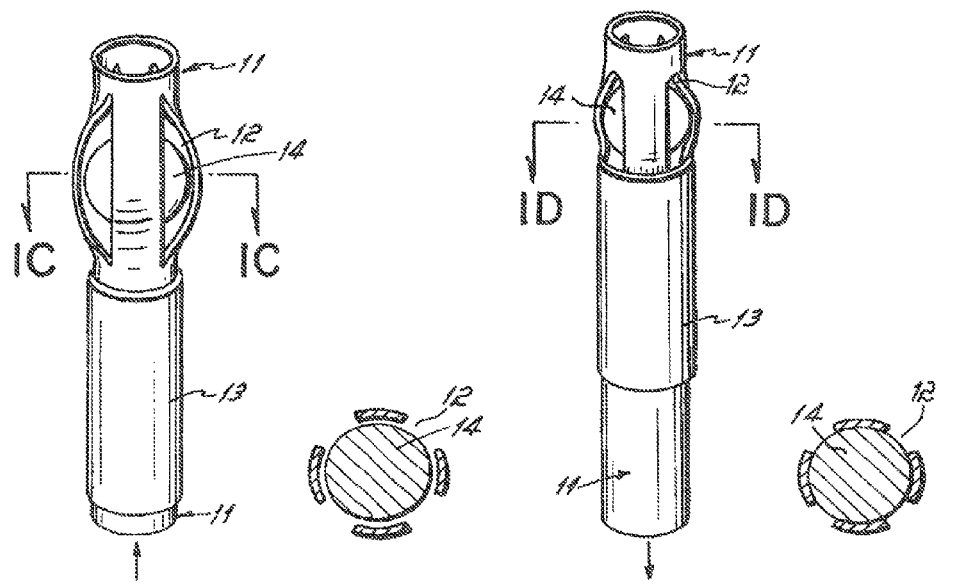
FIGS. 1A and 1B are pictorial views of a retrieval basket of the present invention.
FIGS. 1C and 1D are cross-sectional views taken along lines 1C-1C and 1D-1D of FIGS. 1A and 1B, respectively.

FIGS. 1A and 1B show a memory metal tube 11 with four slots 12 near the distal end. The slots 12 create a balloon-shaped structure which can be used as a retrieval basket for small particles 14, with a closure around the caught particle due to the concave shape of the inner wall of the memory metal tube 11. As shown in FIGS. 1A to 1D, particle 14 is a solid particle. Dependent on the application, either the delivery tube 13 or the memory metal tube is moved, but in both cases the relative axial movement enables the expansion or the contraction of the memory metal tube. The single piece construction is far more simple than with conventional baskets made of several pieces that have to be connected. The advantage of the concave surface can be seen in the top views 1C and 1D. In the case of activation by heat, the use of a delivery tool is not necessarily required. With a warm liquid pumped into the memory metal tube, it can be activated (expanded) and with cold fluid it can be brought into the martensitic, deformed state again (contracted).

Dilation Tool

Figures 2, 3, 4:
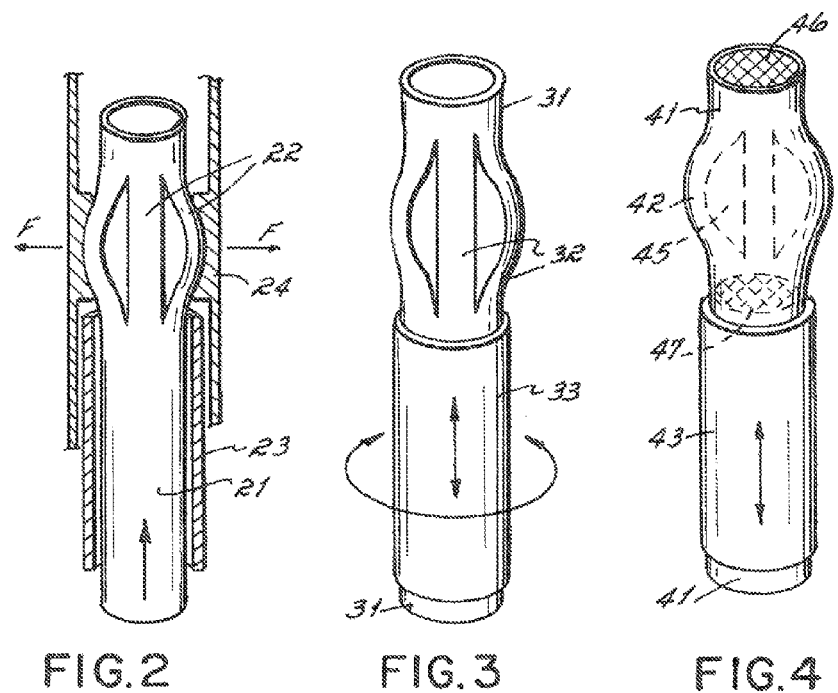
FIG. 2 is a partial sectional pictorial view of a dilation tool of the present invention.
FIG. 3 is a pictorial view of a reamer of the present invention.
FIG. 4 is a pictorial view of a micropump of the present invention.

FIG. 2 shows a tool for dilation of tubular structures such as vessels 24 where the wall thickness of the capillary memory metal tube 21 and the geometry of the segments 22 determine the dilation force F. The delivery tube 23 can be kept in place and the memory metal dilator with the desired dilation force can be inserted. Several dilators with increasing force can be inserted to gradually increase the inner diameter of the artery or cavity. The memory metal tube can either be heated to increase the force and/or diameter, or it can be used super-elastically where the well defined plateau stresses give a predetermined and known force. Conventional dilation techniques use a series of tools with increasing diameters, which work less efficiently in many cases.

Reamer

FIG. 3 shows a reamer where the edges 32 of the slotted section have been sharpened. By relative axial movement of the memory metal tube 31 and delivery tube 33, the diameter of the reamer is continuously variable. By relative tangential movement (rotation) of the reamer in the delivery tube, the sharp edges of the expanded section cut particles of the inner wall of the artery or any other tubular or other shaped cavity.

Micropump

FIG. 4 shows a small micropump for the local injection of a well defined quantity of fluid. An example of such a fluid would be a dissolution fluid for obstructions in arteries or kidney stones. The slotted section 42 of the metal tube 41 creates a balloon shaped room 45 with a specific volume. The slotted section 42 is expandable and either surrounds or is surrounded by an elastic material in the shape of a balloon. Two one way valves 46 and 47 above and below the balloon section and connected to its distal and proximal ends, respectively, enable a pumping action in the distal direction by advancing the delivery tube 43 over the slotted section 42 of metal tube 41. This decreases the volume. Both valves are opening in the same direction and by moving in and out (as shown by the arrows) the balloon pump and deliver one shot of liquid repeatedly.

Optical System with Expander

Figure 5:
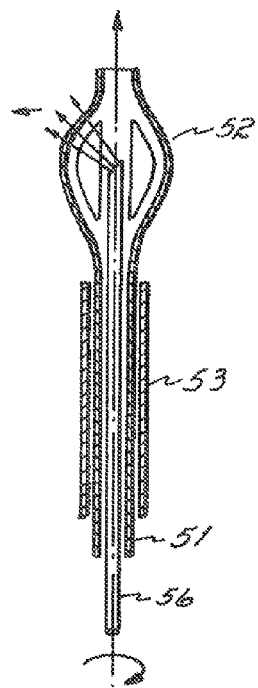
FIG. 5 is a partial sectional pictorial view of an optical system with expander of the present invention.

FIG. 5 shows a memory metal tube 51 with an expanding section 52 that can contain an optical fiber 56 in the center, with the free end of the fiber in the center of the expanding section 52, thus enabling an inspection of this expanded area and adjacent areas. The ratio between constrained and expanded diameter can be very large (e.g., a factor of 10), which makes it possible to inspect cavities that are more or less collapsed or deformed. The inner wall of the expanded cavity can be observed as well as the area in front of the tip as shown by the multidirectional arrows. This tool can be used for gynealogics, urethra, ear, nose, arteries, biliaric, esophageal inspections in cavities and/or cylindrical rooms, etc. Another feature of this device is the exact fixation of the inspection fiber(s) in the center of the cavity. A delivery tube 53 can also be utilized to control the expansion of the expanding section 52.

Internal Gripper

Figure 6A:
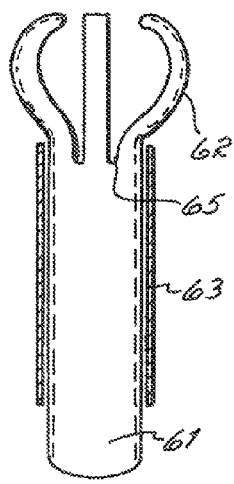
FIGS. 6A and 6B are partial sectional pictorial views of an internal gripper of the present invention.
Figure 6B:
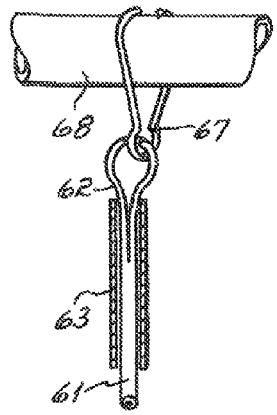

FIG. 6A shows a memory metal tube 61 with slots 65 that proceed to the distal end of the tube. The tube end has been programmed into a gripper shape for holding soft tissue like skin, nerves, arteries, clips, etc. When the delivery tube 63 is pushed forward the curved tube segments 62 close toward the center axis of the instrument. In the case of use with clips, a double hook such as that shown in FIG. 6B is used to hold a surgical memory metal clip 67, bring it over the artery 68, fallopian tube, oviduct, or nerve that has to be held by the clip, heat the clip to close it over the artery by means of a warm fluid inserted through the memory metal tube. After closing of the clip, the delivery tube 63 is moved back to open the hooks again, leaving the clip where it is. Then the gripper is closed again and the tool is pulled back.

External Gripper

Figure 7A:
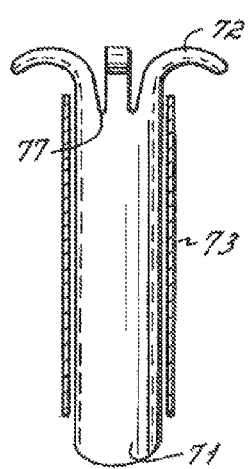
Figure 7D:
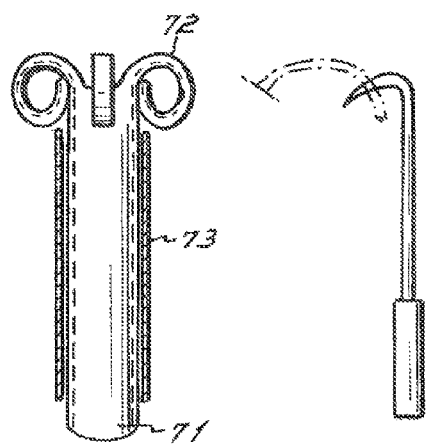
Figure 7D:
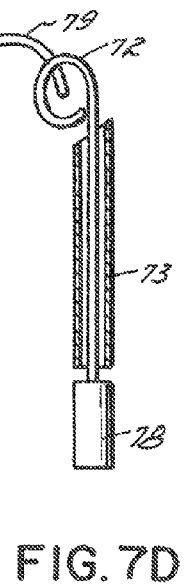

Similar to the previous example of an internal gripper, FIGS. 7A and 7B show an external gripper in which the slots 77 proceed to the free end of the memory metal tube 71. Now the curved segments 72 have been programmed to curve into an outward direction. FIG. 7A shows a gripper that can catch a lost or migrated stent from the inside to move it in a longitudinal direction. FIG. 7B shows a gripper with segments 72 that are programmed to make a closed loop against the outside wall of the delivery tube 73. When the tip of each section is sharpened, these sections can cut themselves a path through soft tissue. This enables the use as a connector, that holds itself tightly to the soft tissue, because of its geometry. Such a connector can be the tip of a pacemaker lead or an electrode for measuring or electrical stimulation, e.g., for potential measurements in the inner wall of the stomach. FIG. 7C gives an example of a conventional skin hook that holds a wound open during surgery. Sometimes these skin hooks fall off. Superelastic skin hooks using a closed loop 72 do not fall off so quickly, because they lock the skin completely in their closed loop. In this construction, as seen in FIG. 7D, the delivery tube 73 can have the shape of a hollow needle with a sharp point. Eventually a weight 78 is attached to the opposite end from the loop 72 to keep the skin 79 open.

Expander

Figure 8:
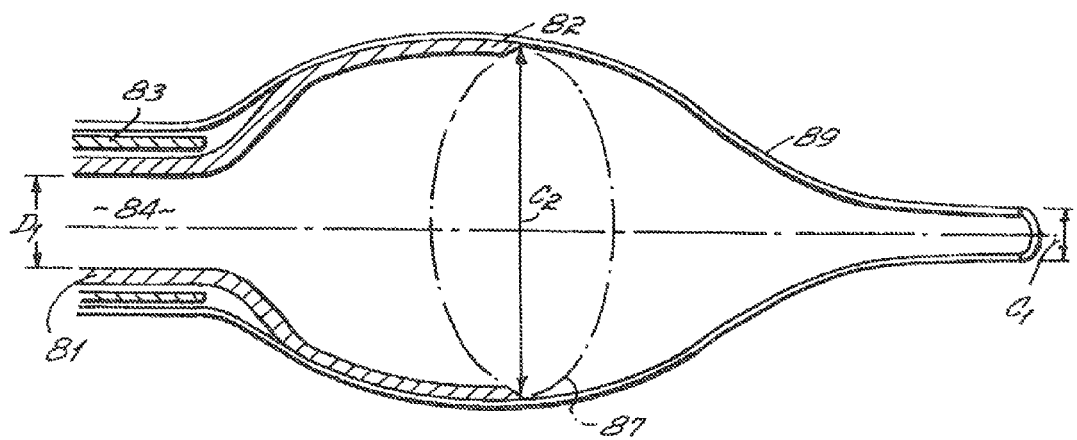
FIG. 8 is a partial sectional pictorial view of an expander of the present invention.

An expansion tool, shown in FIG. 8, is used for difficult accessible cavities where optical information is needed or where a place is required for working with instruments. As contrasted with the expander shown in FIGS. 2 and 5, here the expanding area is at the distal tip 82 of the memory metal tube 81. The expander has a working canal 84 with diameter $D_1$, to enable bringing instruments into the narrow cavity, which now has an expanded area 87. The cavity wall 89 is expanded by the tool from its normal diameter $C_1$ to an expanded diameter $C_2$ to create the expanded area 87.

Expandable Plug

Figures 9A, 9B, 9C:
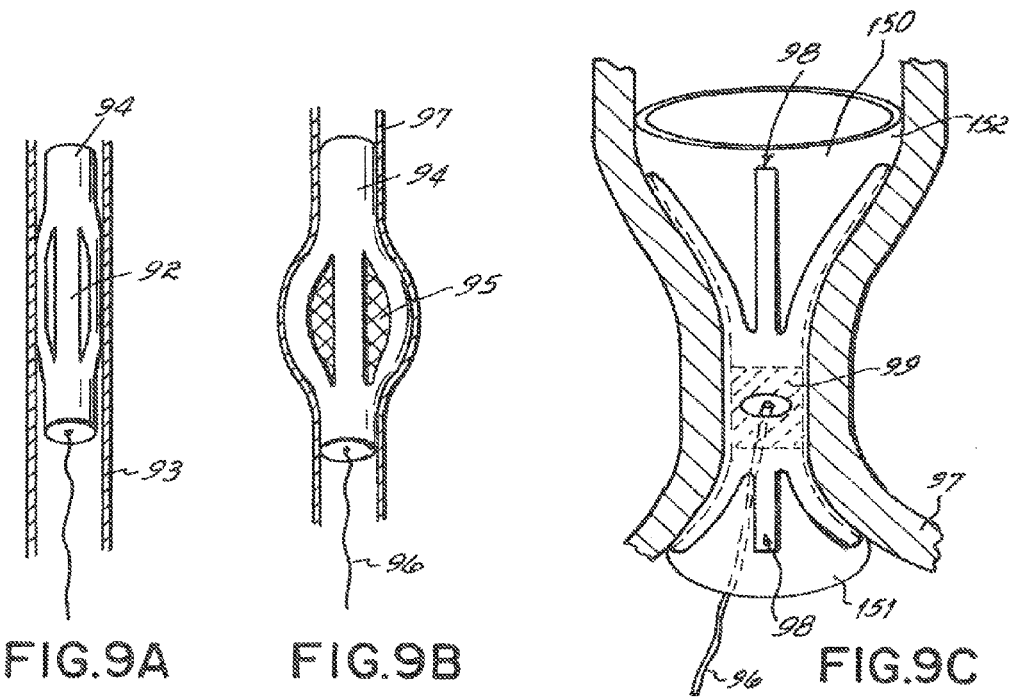
FIGS. 9A through 9C are partial sectional pictorial views of an expandable plug of the present invention.

FIGS. 9A and 9B show a short length of memory metal tube 91 with a slotted section 92 that can be brought into a fallopian tube or oviduct 97 in case of sterilization or any other cavity that is to be closed, either temporarily or permanently. This is done via a delivery catheter 93. When the plug 94 (or sterilization device) is pushed from the delivery catheter 93 into the cavity (such as fallopian tube 97), it will expand and seal the cavity. This is achieved by the combination of the expanded slotted section 92 of plug 94 with an elastic polymer 95 that fills the slotted section 92 in the plug 94. This elastic material has to be able to completely follow the deformation of the plug 94 from collapsed to final size. Eventually, the plug 94 can be filled with a UV-curing material to make it solid by means of a light from a core fiber. At the proximal end of the plug 94, an extraction wire 96 (or hook or eyelet) is provided for withdrawal into delivery tube 93 in case the plug has to be removed again. FIG. 9C shows a chalice-shaped variant of a sterilization device 94 with a slotted tube 150 that has slots at both ends to make a device that can be put into a cavity that has a shape with a smaller diameter in the center area and bigger diameters above and below (i.e., a cavity with a constricted portion). This is the case in the exit side of the oviduct, near the uterus. The center area of the hollow memory metal tube 150 is sealed with a plug 99 having an attached extraction wire 96. The expanded sections 151 and 152 of tube 150 can be combined with an elastic polymer (not shown) that finishes the chalice shape to result in less irritation of the adjacent tissue and to get a better sealing against the wall of the oviduct 97.

Measuring Tip

The reamer of FIG. 3 or the expander of FIGS. 2 and 5 can also be combined with an optical or mechanical means to measure the diameter of the cavity at any position near the distal end of the tube, such as an artery wall 10. This can be achieved in several ways. FIG. 10A shows a memory metal tube 101 with an expanding section 102 and a delivery tube 103. The memory metal tube 101 itself acts as a delivery tube for a third tube 107 that contains an optical system 106 that looks forward from the distal tip 109 for visual inspection (as represented generally by the arrows), and provides a light image.

An alternative embodiment is shown in FIG. 10B where the memory metal tube 101 holds a delivery tube 107 with a superelastic measuring wire 108 in the center thereof, that has been programmed to make a curvature at the tip when it leaves the restraining tube 107. With a scale readout at the proximal side of the catheter/endoscope, the radius of the cavity at the measuring spot can be seen by determining the moment that the bending tip touches the inner wall.

In FIG. 10C, a third variant is shown with a hollow superelastic wire 108 that has been programmed in the same way as described above with respect to FIG. 10B. In this embodiment, the hollow wire 108 contains an optical system 111, thus combining the optical readout with a bending tip. This improves the accuracy, because the light emitter/sensor 109 comes closer to the wall than in the situation described under FIG. 10A.

Steerable Tip

A steerable catheter tip can be made by means of a slotted memory metal tube, where the slots are made in such a way that a contraction or expansion of a part of the wall can be achieved by local temperature changes. There are many options for the shape of expanding or contracting sections. Pure bending of one or more segments of the wall can also be used to make the tip steerable. In FIG. 11, one example is given of a memory metal tube 201 with slots 202 in a zigzag pattern to enlarge the possible contraction per segment 203, when it is heated to give an angular deviation of the top portion 204 compared to the central axis of the lower portion of the memory metal tube 201. Heating can also be achieved in several ways, such as local light from a light source or resistance heating. The latter can either be indirect by heating a resistance film that is attached to the memory segment 202, or by direct resistance heating of the memory metal. In the latter case, the segment 202 must at least at one end be electrically isolated from the rest of the memory metal tube. This can be done by letting the zigzag slots run to the free end of the distal tip (not shown), where the electrical leads can be connected to the end of any single segment 202.

Reinforced Stent

A UV-curing polymer is used to make a stent very flexible during insertion and then let it solidify by light emission. A double-walled balloon with the UV curing polymer in-between is already on the market. However, in some cases, it would be an improvement to reinforce this type of stent with an integrated memory metal stent based on the principle of a slotted memory metal tube to make the construction more stable. FIGS. 12A and 12B give a view of the cross section through a combined stent in collapsed and expanded shape, respectively. The UV-curing balloon stent 303 is reinforced with segments 302 of a memory metal tube. The slots in the memory metal tube are made in such a pattern that the stent is expandable.

Although several embodiments of the present invention have been illustrated in the accompanying drawings and described in the foregoing Description of the Preferred Embodiments, it will be understood that the invention is not limited to the embodiments disclosed but is capable of numerous rearrangements, modifications, and substitutions of parts and elements without departing from the spirit and scope of the invention. In some cases the tube can exist from several segments that run through the entire length from proximal to distal. This can be necessary if there has to be an electrical isolation between the expandable segments, like in the application of an electrode for measuring potential and/or electrical stimulation of body parts.

The direction of the slots has been parallel to the longitudinal axis of the memory metal tube in the embodiments described above, but they can also be cut into the wall in alternative directions to achieve better performance. An example would be a retrieval basket with helical shaped segments. Further, it can be necessary to use more than one concentric tube with varying functions. Non-concentric tubes, which can be placed beside one another, parallel in the delivery tube, are also embodiments of the present invention.

What is claimed is:

1. A medical device for use within a tubular structure of a human body, the device comprising:

at least one monolithic memory metal tube configured and sized to be inserted within the tubular structure of the human body, the metal tube including at least one expandable section with a plurality of metal members separated by openings, the plurality of metal members being pre-programmed for a shape-memory effect based on a transformation temperature, the metal members expanding from a contracted shape to an expanded shape at or above the transformation temperature to form a retrieval basket for retrieving particles to be removed from the human body, each of the metal members being sufficiently rigid to substantially maintain the expanded shape of the expandable section when placed within and in contact with the tubular structure of the human body, the expandable section being free of interior structure that is axially movable within the expandable section to expand and/or contract the expandable section, the metal tube having a central longitudinal axis and a distal end, the expandable section being configured to catch a solid particle having a maximum cross-sectional dimension greater than a maximum cross-sectional dimension of the distal end of the metal tube transverse to the central longitudinal axis of the metal tube.

2. The device of claim 1, further comprising an outer tube surrounding the metal tube, the outer tube being slidable over the expandable section and configured to restrict the expandable section to the contracted shape.

3. The device of claim 1, wherein the expanded shape is a shape programmed using the memory effect of the metal tube.

4. The device of claim 3, wherein the programming of the shape is accomplished through a heat treatment of the metal tube.

5. The device of claim 1, wherein the tubular structure of the human body is a blood vessel.

6. The device of claim 1, wherein the tubular structure of the human body is a urethra.

7. The device of claim 1, wherein the metal tube has only a single lumen.

8. The device of claim 1, wherein the metal tube has a proximal end and a longitudinal passage with a central longitudinal axis coaxial to the central longitudinal axis of the metal tube.

9. The device of claim 1, wherein the openings are slots forming a slotted section, the slotted section being bounded by two non-slotted sections.

10. The device of claim 1, wherein the openings each have a mid-longitudinal axis and a complete perimeter surrounding the mid-longitudinal axis.

11. The device of claim 1, wherein the plurality of metal members are deformed in a martensitic state to the contracted shape.

12. The device of claim 1, wherein the metal members remain in the contracted shape below the transformation temperature independent of mechanical influences by any material external to the metal members.

13. The device of claim 1, wherein the plurality of metal members are activated by heat to form the expanded shape.

14. The device of claim 1, wherein the plurality of metal members are activated to form the expanded shape without the use of a delivery tool.

15. The device of claim 14, wherein the delivery tool is an outer tube.

* * * * *